United States Patent [19]

Brown et al.

[11] Patent Number: 5,284,994
[45] Date of Patent: Feb. 8, 1994

[54] INJECTION OF ANTIFOULANTS INTO THERMAL CRACKING REACTORS

[75] Inventors: Ronald E. Brown; K. James Sasaki; Larry E. Reed, all of Bartlesville, Okla.

[73] Assignee: Phillips Petroleum Company, Bartlesville, Okla.

[21] Appl. No.: 4,391

[22] Filed: Jan. 13, 1993

[51] Int. Cl.$^5$ .............................................. C07C 4/04
[52] U.S. Cl. .................................. 585/648; 585/950; 208/48 AA; 208/106; 208/130; 208/132
[58] Field of Search ............................. 585/648, 950; 208/48 AA, 106, 130, 132

[56] References Cited

U.S. PATENT DOCUMENTS

| | | | |
|---|---|---|---|
| 3,132,085 | 5/1964 | Summers, Jr. | 208/48 AA |
| 4,024,048 | 5/1977 | Shell et al. | 585/866 |
| 4,404,087 | 9/1983 | Reed et al. | 208/48 AA |
| 4,507,196 | 3/1985 | Reed et al. | 208/48 AA |
| 4,545,893 | 10/1985 | Porter et al. | 208/48 R |
| 4,551,227 | 11/1985 | Porter et al. | 208/48 AA |
| 4,552,643 | 11/1984 | Porter et al. | 208/48 AA |
| 4,666,583 | 5/1987 | Porter et al. | 208/48 AA |
| 4,687,567 | 8/1987 | Porter et al. | 208/48 AA |
| 4,692,234 | 9/1987 | Porter et al. | 208/48 AA |
| 4,889,614 | 12/1989 | Forester | 585/650 |
| 5,015,358 | 5/1991 | Reed et al. | 208/48 AA |

Primary Examiner—Anthony McFarlane
Attorney, Agent, or Firm—K. K. Brandes

[57] ABSTRACT

A liquid tin-containing antifoulant composition is injected into a metal-walled thermal cracking reactor tube, concurrently with the injection of a gaseous stream (preferably a steam-diluted $C_2$-$C_4$ alkane stream), through a nozzle of an injection quill which is positioned in the center region of the reactor tube substantially parallel to the flow of the gaseous stream.

A liquid tin-containing antifoulant is injected into a metal-walled thermal cracking reactor tube through a nozzle of an injection quill at a temperature of about 1000°-1300° F. while a gaseous stream (preferably a steam-diluted $C_2$-$C_4$ alkane stream) flows through the reactor tube, followed by raising the temperature to about 1400°-1800° F. Preferably, the metal walls of the reactor tube are treated with steam after the antifoulant injection at about 1000°-1300° F. but before the antifoulant injection at about 1400°-1800° F.

22 Claims, 2 Drawing Sheets

INJECTION OF ANTIFOULANTS INTO THERMAL CRACKING REACTORS

BACKGROUND OF THE INVENTION

This invention relates to methods of injecting tin-containing antifoulants into thermal cracking (pyrolysis) reactors, so as to alleviate the undesirable formation of coke and carbon monoxide during thermal cracking of light hydrocarbons. In a particular aspect, this invention relates to injecting tin-containing antifoulants into ethane cracking reactors (for making ethylene).

Numerous tin-containing antifoulant agents for reducing the formation of coke on the metal walls of light hydrocarbon pyrolysis (thermal cracking) reactors are known and have been described in the patent literature, such as U.S. Pat. Nos. 4,404,087, 4,507,196, 4,545,893, 4,551,227, 4,552,643, 4,666,583, 4,687,567, 4,692,234 and 5,015,358. These tin-containing antifoulants (either dissolved tin compounds or mixtures of dissolved tin and other compounds) can be injected into a hydrocarbon-containing feed, or they can be used to pretreat (coat) the inner metal walls of a thermal cracking reactor (before the hydrocarbon-containing feed is introduced into the cracking reactor), or both. The present invention is directed to novel methods of injecting tin-containing antifoulants into thermal hydrocarbon cracking reactors, either before or during the thermal cracking of hydrocarbons, so as to alleviate the deposition of coke on metallic reactor walls and the generation of carbon monoxide.

SUMMARY OF THE INVENTION

It is an object of this invention to provide effective methods of injecting a liquid tin-containing antifoulant into a gas flowing through a metal-walled thermal cracking (pyrolysis) tube reactor. It is another object of this invention to provide an effective method of injecting a liquid tin-containing antifoulant into a hydrocarbon-containing feed gas flowing through a metal-walled thermal cracking tube reactor. It is a further object of this invention to treat the metal walls of a thermal hydrocarbon cracking reactor after the injection of a liquid tin-containing antifoulant into said reactor but before thermal cracking of the feed hydrocarbon(s) occurs. It is a still further object of this invention to provide effective methods of injecting a liquid tin-containing antifoulant into a thermal cracking reactor, before and during the thermal cracking of a hydrocarbon feed gas, so as to alleviate coke and/or carbon monoxide formation during thermal hydrocarbon cracking. Additional objects and advantages will be apparent from the detailed description of this invention and the appended claims.

In accordance with the first embodiment of this invention, in a process for injecting a liquid tin-containing antifoulant composition into a metal-walled thermal cracking (pyrolysis) reactor tube concurrently with the introduction of a gaseous stream, the improvement comprises injecting the liquid antifoulant composition into said reactor tube through a nozzle of an injection quill which is positioned substantially parallel to the flow of said gaseous stream and extends into the center region of said reactor tube at a distance equal to at least the diameter of said reactor tube. Preferably, the gaseous stream is a feed stream comprising at least one saturated hydrocarbon containing 2-12 carbon atoms per molecule. Also preferably, the conditions in said reactor tube are such as to affect thermal cracking of said at least one saturated hydrocarbon (more preferably alkane) to at least one unsaturated hydrocarbon (more preferably alkene).

In accordance with the second embodiment of this invention, in a process for injecting a liquid tin-containing antifoulant composition into a metal-walled thermal cracking reactor tube, the improvement comprises:

(1) passing a gaseous stream through the reactor tube while simultaneously injecting the liquid tin-containing antifoulant composition through a nozzle of an injection quill into the reactor tube at a temperature of about 1000°-1300° F. (preferably about 1200°-1300° F.); and (2) raising the temperature in the reactor tube from the operating temperature of step (1) to a temperature of about 1400°-1800° F. (preferably about 1450°-1550° F.), while maintaining the injection of the liquid antifoulant composition into and the flow of the gaseous stream through said reactor.

Preferably, the gaseous stream is a feed stream comprising at least one saturated hydrocarbon containing 2-12 carbon atoms per molecule. Essentially no thermal cracking of the at least one saturated hydrocarbon occurs in step (1), whereas thermal cracking of the at least one saturated hydrocarbon (more preferably alkane) to at least one unsaturated hydrocarbon (more preferably alkene) occurs in step (2). Also preferably, this second embodiment of the invention is carried out in accordance with the antifoulant injection method of the first embodiment of this invention (described above).

Another preferred feature of this second embodiment comprises the following additional steps after step (1) but before step (2):

(1A) interrupting the injection of the liquid antifoulant composition and the flow of the gaseous stream, (1B) introducing steam into the reactor tube for at least about 60 minutes (preferably about 1-5 hours) at a temperature of about 1000°-1300° F. (generally at a rate of about 1-5000 lb/hour, depending on reaction tube dimensions), (1C) interrupting the flow of steam, and (1D) resuming the injection of the liquid antifoulant composition and the flow of the gaseous stream.

DETAILED DESCRIPTION OF THE INVENTION

Figure 1:
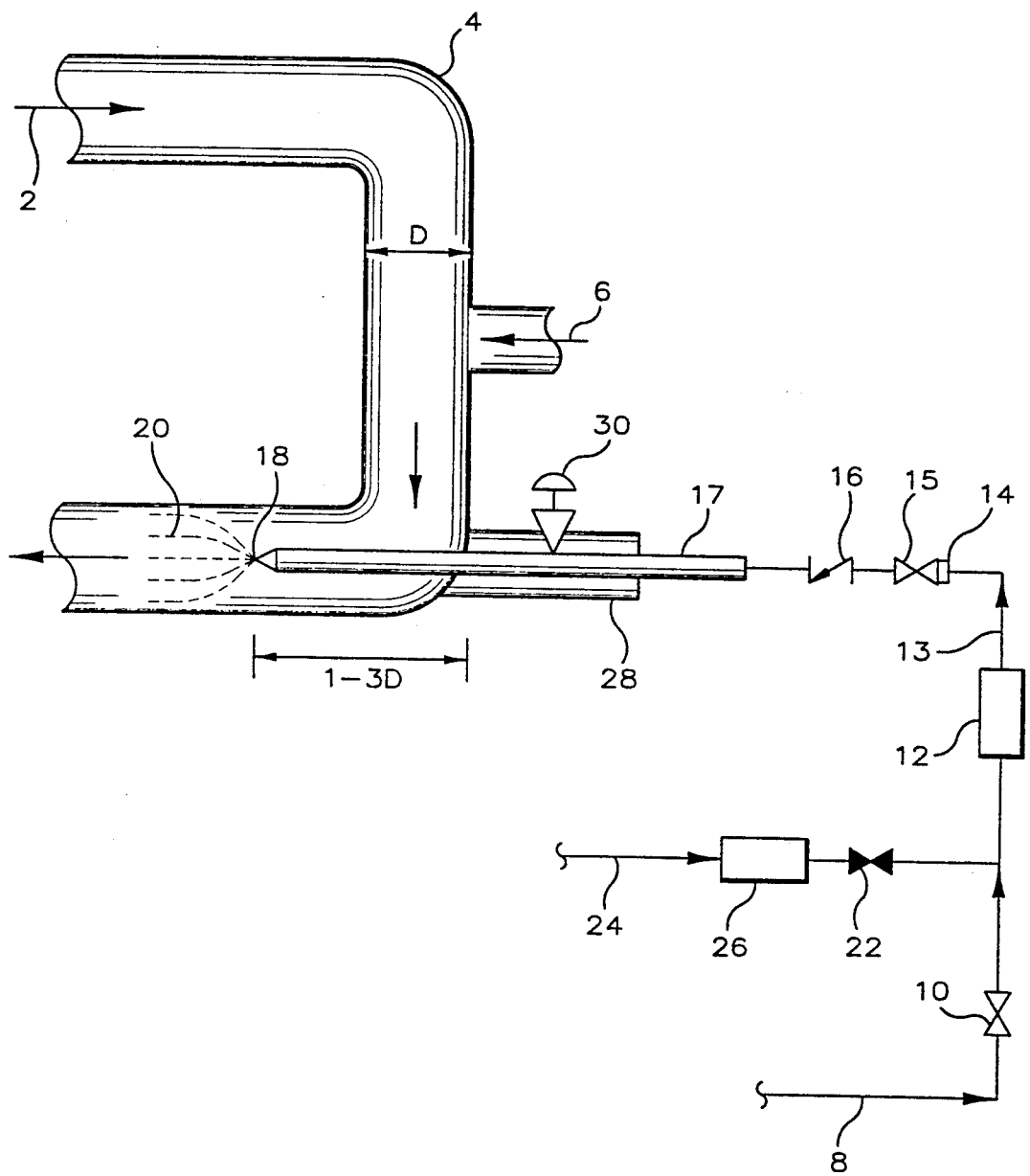
FIG. 1 illustrates a preferred method for injecting a tin-containing antifoulant solution into a hydrocarbon/steam gas mixture which flows through a thermal cracking tube reactor.

The term "coke", as used herein, refers to any form of carbon having any degree of purity which is deposited on metal walls during exposure to a hydrocarbon-containing feed gas under thermal cracking (pyrolysis) conditions. A portion of the "coke" can be converted to carbon monoxide in the presence of steam. The term "metal wall(s)" or "metal-walled", as used herein, refers to any wall made of a metallic material on which hydrocarbons are partially converted to coke and also to carbon monoxide (when steam is present), under thermal hydrocarbon cracking conditions. The metallic material can contain iron, nickel, copper, chromium, molybdenum, manganese and the like. Example of such metallic materials include alloys such as Inconel 600, Incoloy 800, HK-40 stainless steel, 304SS stainless steel (all described in U.S. Pat. No. 4,404,087, Column 5), and the like. Generally, the iron content of these metallic alloys is less than about 98 weight-%, and preferably ranges from about 8 to about 95 weight percent Fe. The terms "reactor" and "reactor tube", as used herein, refer to any metal-walled portion of the thermal cracking reactor system which is exposed to hydrocarbon(s) at thermal cracking conditions, and encompasses the main reaction chamber (cracking tube), conduits leading to and from the reaction chamber, heat exchangers, and the like.

The term "thermal cracking" or "pyrolysis", as used herein, implies that saturated hydrocarbons (i.e., straight-chain alkanes, branched alkanes and cycloalkanes) which are gaseous at the thermal cracking conditions are at least partially dehydrogenated to the corresponding olefins (in particular alkenes and cycloalkenes). The feed hydrocarbons can contain from 2 to about 12 (preferably 2-8) carbon atoms per molecule, and include ethane, propane, butanes, pentanes, hexanes, heptanes, octanes, nonanes, decanes, cyclopentane, cyclohexanes, methylcyclopentanes, cycloheptane, dimethylcyclopentanes, ethylcyclopentane, methylcyclohexanes, cyclooctanes, trimethylcyclopentanes, methylethylcyclopentanes, dimethylcyclohexanes, ethylcyclohexane, methylcycloheptane, dimethylcycloheptanes, ethylcycloheptane, trimethylcycloheptanes, methylethylcycloheptanes, and the like. The preferred hydrocarbons used as feed hydrocarbons are ethane, propane and butanes (n-butane and/or isobutane), which are thermally cracked to the corresponding alkenes (ethylene, propylene, butene-1, butene-2 and isobutylene). Generally, the feed gas also contains steam (as a diluent), preferably at a steam:hydrocarbon mole ratio (=volume ratio) of about 0.1:1 to about 1.5:1, more preferably of about 0.25:1 to about 0.75:1. The hydrocarbon content in the feed gas generally is in the range of about 40 to about 90 volume-%.

Any suitable thermal hydrocarbon cracking equipment and conditions can be employed. Generally the thermal cracking reactor is a metal tube having an inner diameter of about 1-6 inches and a total length of about 25-500 feet. The cracking tube can be straight, bent or looped. Suitable thermal cracking conditions are well known to those skilled in the art. Optimal cracking conditions can easily be determined by those skilled in the art, and depend on the feed hydrocarbon(s), the desired process cycle times (i.e., the time from the start of the thermal cracking process cycle to its interruption for oxidative decoking of the reactor), the flow rate (residence time in the reactor) of the feed hydrocarbon(s), the dimensions of the reactor and of conduits and heat exchangers, the desired product composition, and the like. In the preferred thermal cracking of light hydrocarbons (such as ethane, propane, n-butane, isobutane) in the presence of steam, the temperature in the cracking reactor generally is in the range of about 1350° C. to about 1800° C., the pressure (at the reactor outlet) generally is about 2-40 psig, and the residence time of the hydrocarbon/steam feed in the cracking reactor generally is about 0.1-1.5 seconds. Generally, the hydrocarbon/steam feed is preheated (preferably to about 1000°-1200° F.) before it is introduced into the cracking reactor, which is heated to the cracking temperature by means of external furnace(s).

Any suitable tin compound can be utilized as an antifoulant in the processes of this invention. Inorganic tin compounds and organic tin compounds, as well as mixtures of any two or more tin compounds, are suitable sources of tin. The term "antifoulant", as used herein, means that the antifoulant material is effective in alleviating the formation of coke (deposited on metal walls), or the generation of carbon monoxide (which is probably formed by the reaction of steam with formed coke: $H_2O + C = CO + H_2$), or the formation of both coke and carbon monoxide during thermal cracking of the feed hydrocarbon(s).

Examples of some inorganic tin compounds which can be used include tin oxides such as stannous oxide and stannic oxide; tin sulfides such as stannous sulfide and stannic sulfide; tin sulfates such as stannous sulfate and stannic sulfate; stannic acids such as metastannic acid and thiostannic acid; tin halides such as stannous fluoride, stannous chloride, stannous bromide, stannous iodide, stannic fluoride, stannic chloride, stannic bromide and stannic iodide; tin phosphates such as stannous phosphate and stannic phosphate; tin oxyhalides such as stannous oxychloride, stannic oxychloride and the like. Tin dioxide, especially in form of a colloidal dispersion in water (or another suitable liquid), is a particularly suitable inorganic tin antifoulant.

Examples of some organic tin compounds which can be used include tin carboxylates such as stannous formate, stannous acetate, stannous butyrate, stannous octanoate (in particular stannous 2-ethylhexanoate), stannous decanoate, stannous benzoate, and stannous cyclohexanoate; tin thiocarboxylates such as stannous thioacetate and stannous dithioacetate; dihydrocarbyltin bis(hydrocarbyl mercaptoalkanoates) such as dibutyltin bis(isooctyl mercaptoacetate) and dipropyltin bis(butylmercaptoacetate); tin thiocarbonates such as stannous O-ethyl dithiocarbonate; tin carbonates such as stannous propyl carbonate; tetrahydrocarbyltin compounds such as tetrapropyltin, tetrabutyltin, tetrahexyltin, tetraoctyltin, tetradodecyltin and tetraphenyltin; dihydrocarbyltin oxides such as dipropyltin oxide, dibutyltin oxide, butylstannoic acid, dioctyltin oxide and diphenyltin oxide; tin bis(hydrocarbylmercaptide) such as tin bis(dodecylmercaptide); tin salts of phenolic or thiophenolic compounds such as stannous phenoxide and stannous thiophenoxide; tin carbamates such as stannous diethylcarbamate; tin thiocarbamates such as stannous propylthiocarbamate and stannous diethyldithiocarbamate; tin phosphites such as stannous diphenyl phosphite; tin phosphates such as stannous dipropylphosphate; tin thiophosphates such as stannous O,O-dipropyl thiophosphate, stannic O,O-dipropyl dithiophosphate; dihydrocarbyltin bis(O,O-dihydrocarbyl thiophosphate)s such as dibutyltin bis(O,O-dipropyl dithiophosphate); and the like. Organic tin compounds (which are thermally converted to tin dioxide) are presently preferred antifoulants. Presently most preferred is tetra-n-butyltin.

Generally, the tin-containing antifoulant is dissolved (or colloidally dispersed) in a suitable solvent. Any suitable solvent can be utilized to prepare antifoulant solutions (which may be colloidal solutions/dispersions). Suitable solvents include water (in particular for inorganic tin compounds); oxygen-containing organic liquids such as alcohols, ketones and esters; and (in particular for organic tin compounds) liquid aliphatic or cycloaliphatic or aromatic hydrocarbons or mixtures thereof, preferably heptane. The terms "colloidal dispersion" and "colloidal solution" are synonymous and are interchangeably used herein. These terms, as used herein, refer to dispersions of particles (in particular $SnO_2$) having a particle diameter in the range of from about 10 to about 2,000 angstroms (i.e., about $1-200\times10^{-9}$ m).

Any suitable concentration of the tin compound(s) in the antifoulant solution (or colloidal dispersion) can be utilized. Generally, the concentration of tin compound(s) is at least about 0.01 mole/l, but may be about 1.5 mole/l (or higher, with the concentrations being limited by the solubility of a particular tin compound in a particular solvent and by metallurgical and economic considerations). The presently preferred concentration of tin compound(s) in the solution (or colloidal dispersion) is in the range of about 0.02 mole/l to about 1.0 mole/l.

Even though the use of at least one dissolved tin compound alone as antifoulant in the process of this invention is presently preferred, it is within the scope of this invention to employ dissolved mixtures of tin compound(s) and at least one other compound which is effective as an antifoulant, such as compounds of antimony, germanium, chromium, aluminum, phosphorus, copper, gallium, indium, silicon and titanium, examples of which are disclosed in the above-cited U.S. patents. Of these additional antifoulant compounds (which can be used in addition to at least one tin compound), compounds of silicon, aluminum and titanium are presently preferred (because they are environmentally most acceptable).

Presently preferred particular additional antifoulant compounds include oxides of Al, of Si and of Ti, which are generally used in combination with tin dioxide in aqueous colloidal dispersions; alcoholates of Al and Ti (such as aluminum isopropoxide and titanium n-butoxide) and orthosilicates (such as tetraethylorthosilicate), all of which are generally used in combination with organic tin compound(s) and are dissolved in an organic solvent. The concentrations of each additional antifoulant compound in an antifoulant solution or colloidal dispersion generally is at least about 0.04 mole/l, preferably about 0.3-0.6 mole/l. When combinations of at least one tin compound and at least one other antifoulant compounds are used, any suitable weight percentage of each antifoulant in such combinations can be employed. Generally, such antifoulant combinations contain at least about 30 mole-% of tin compound(s). Preferably, the antifoulant contains about 30-100 weight-% tin compound(s), and about 0-70 weight-% additional antifoulant compound(s), based on the weight of the antifoulant (without a solvent).

The antifoulant concentration in the antifoulant solution or colloidal dispersion (preferably a 0.04-1.0 molar solution of tetrabutyltin in heptane) and the antifoulant injection rate into the steam-diluted hydrocarbon feed gas are generally selected such as to provide a tin concentration in the steam-diluted feed gas of at least about 0.5 ppmv tin (i.e., at least about 0.5 part by weight Sn per million parts by volume of feed gas). Preferably, a tin concentration in the feed gas of about 1 to about 200 ppmv Sn is provided. More preferably, the tin level in the feed gas is about 5-100 ppmv Sn. When an additional antifoulant compound is also injected into the gaseous feed, the antifoulant concentration and the injection rate are generally chosen such as to provide a concentration of at least about 0.2 ppm, preferably about 1-100 ppm, of each additional antifoulant element (preferably Si, Al, Ti or mixtures thereof) in the gaseous feed.

The following examples are presented to further illustrate the invention and are not to be construed to unduly limit the scope of this invention.

EXAMPLE I

A preferred embodiment of injecting a tin-containing antifoulant solution or colloidal dispersion through a nozzle into a thermal cracking reactor of tubular shape is illustrated in FIG. 1. A preheated hydrocarbon/steam feed gas stream 2 is introduced into a thermal cracking tube 4 (inner diameter: about 4 inches). Additional dilution steam can be added through pipe 6. An antifoulant solution 8 is pumped through open valve 10, filter 12, tubing 13, tubing connection 14, block valve (ball valve) 15, check valve 16, movable injection quill 17 (having an inner diameter of about 0.18 inch) and injection nozzle 18 (having a radial opening of about 0.025 inch) into the steam-diluted hydrocarbon gas stream. The formed atomized antifoulant spray 20 has the same flow direction as the hydrocarbon/steam gas stream in the cracking tube. The quill nozzle 18 extends into the tube reactor at a distance of about 1-3 times the tube diameter.

If the antifoulant injection is to be stopped, valve 10 is closed, previously closed valve 22 is opened, and an inert purge gas (such as $N_2$ or He) 24 is pumped through filter 26, valve 22, filter 12, tubing 13, tubing connection 14, valves 15 and 16, injection quill 17 and injection nozzle 18 into the cracking tube so as to keep the nozzle from clogging. If in spite of all preventive efforts the injection nozzle clogs, the injection quill 17 can be withdrawn within channel 28 after the flow of the antifoulant liquid and/or inert purge gas has been stopped. When the quill is withdrawn past gate valve 30, this valve is immediately closed. The quill is withdrawn from the outer tube 28 and disconnected from tube 13 at the tubing connection 14, after valves 15 and 16 have been closed. A clean injection quill can then be connected at 14 and moved within channel 28 into reactor tube 4 after valve 30 has been opened. After the other appropriate valves have been opened, antifoulant (or purge gas) can again be pumped through the injection quill into the reactor. Conventional equipment, such as pumps, measurement and control devices, and the like is not shown in FIG. I.

Figure 2:
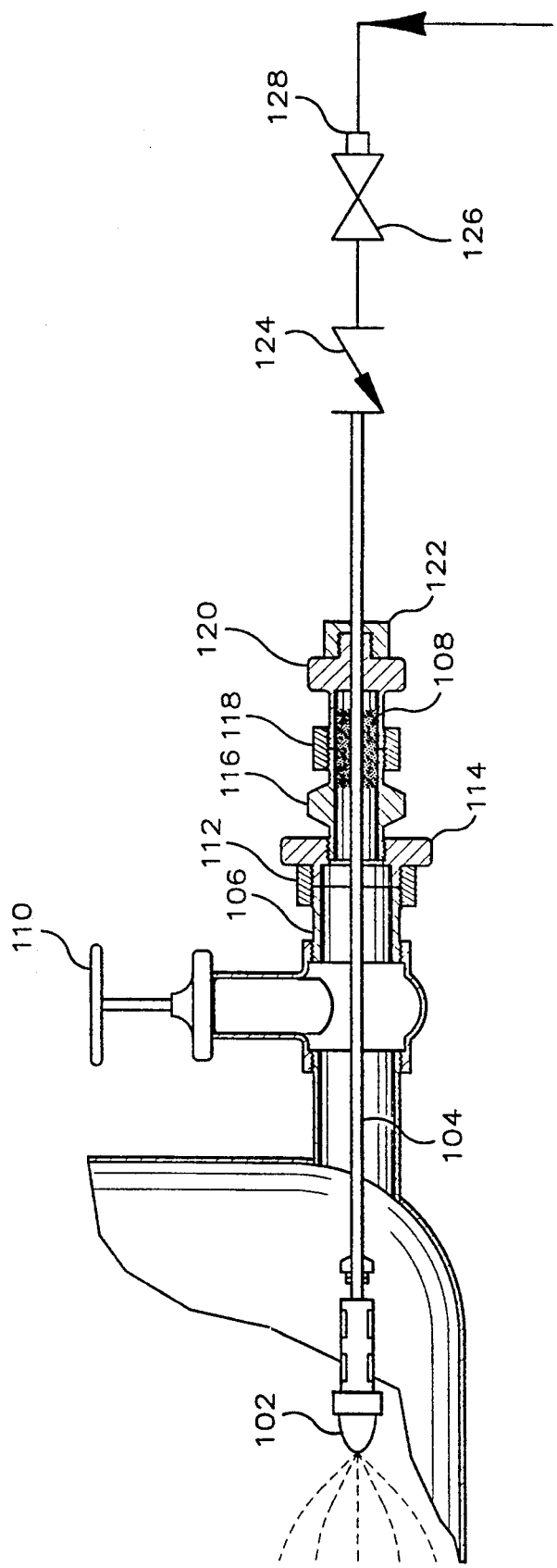
FIG. 2 illustrates a preferred feature for withdrawing an injection quill during the flow of a hydrocarbon/steam gas mixture.

The above-described injection quill is shown in greater detail in FIG. 2. Injection nozzle 102 is located at the end of the injection tube 104 which is made of stainless steel and has a ¼ inch inner diameter. Tube 104 with nozzle 102 is guided into the desired position through steel pipe 106 having an inner diameter of about 1 inch and a length of about 2-3 inches. Graphite packing 108 (around tube 104) prevents any backflow (leakage) of process gases during the antifoulant injection into the reactor tube. Other mechanical parts of the injection system shown in FIG. 2 are: 1-inch full port gate valve 110, collar 112, reducer 114, ½-inch union 116, collar 118, reducing bushing 120, ¼ inch nut 122, check valve 124, block valve (ball valve) 126, and tubing connection 128. When the injection nozzle is clogged and the injection quill is to be withdrawn (so that it can be cleaned or exchanged), the flow of the liquid antifoulant (or of an inert gas) is stopped (as has been described above), the tubing connection 128 is broken, the reducing bushing 120 and nut 122 are loosened, the injection tube 104 with injection nozzle 102 is pulled back past gate valve 110, gate valve 110 is closed, union 116 is disconnected from reducer 114, and pipe 104 is broken at reducer 114. Nozzle 102 and broken pipe 104 can then be pulled out completely, cleaned or replaced with a new nozzle, reinserted into pipe 106, and pushed into the reactor past open gate valve 110. Reducing bushing 120 and nut 122 with attached valve connection 128 are then tightened, and the antifoulant injection can be restarted.

In a preferred commercial operation, the liquid antifoulant composition is a 0.04 molar solution of tetrabutyltin in heptane; the feed hydrocarbon is essentially ethane with steam being present as a diluent; the steam:ethane mole ratio of the feed gas (into which the antifoulant is sprayed) is about 0.45:1 to about 0.55:1; the flow rate of the feed gas is about 6,500–7,500 lb/hour; the residence time of the hydrocarbon/steam mixture in the cracking tube is about 0.1–0.8 seconds (presently preferred: 0.6–0.8 second); and the length of the cracking tube is about 340–360 feet. The temperature profile in the cracking tube is as follows: about 1250° F. in the front (entry) section, about 1450° F. in the middle section and about 1550° F. in the rear (exit) section. Preferably, the hole of nozzle 18 has a diameter of about 0.025 inch so as to provide an exit velocity of the atomized antifoulant spray at 18 of about 100–200 ft/sec.

Even though the residence time of the feed gas in many commercial cracking tubes is presently about 0.6–0.8 second, results of preliminary laboratory tests (not described herein) indicate that the beneficial effect (in terms of alleviating the CO formation during thermal cracking) of the tin-containing antifoulant will be particularly pronounced at even lower feed residence times (as low as about 0.1 second).

EXAMPLE II

This example illustrates the effect of the steam treatment of the inside metal walls of a thermal hydrocarbon cracking tube after the injection of a tin antifoulant solution had been completed but before thermally cracking of the feed hydrocarbon occurred.

A pilot plant cracking tube made of Incoloy 800 stainless steel having an inner diameter of 0.18 inch and a length of 2 feet was heated to a temperature of about 1125° F. A 0.04 molar solution of tetra-n-butyltin in heptane was injected through a nozzle of 0.025 inch inner diameter into the cracking tube at a rate of about 100 cc/hour for a period of time of about 1.7 hours. The total antifoulant dosage was about 3.8 millimoles of tetrabutyltin per hour per ft$^2$ inner surface of the cracking tube.

In one test, steam was thereafter introduced into the antifoulant-coated cracking tube at a rate of 4.5 lb/hour for about 2 hours, while the temperature was increased to about 1250° F. Then the introduction of steam alone was stopped, and a steam/ethane feed gas (molar steam/ethane ration: about 0.5:1; preheated to 1000° F.) was introduced into the antifoulant/steam-treated cracking tube at a temperature of 1680° F. and at a feed rate of 1000 cc/minute (measured at standard temperature/pressure conditions) for a period of time of about 2 hours. The thermally cracked product gas was cooled and analyzed by means of a gas chromatograph. The amount of carbon monoxide generated in this test was 1.5 mole/hour CO per m$^2$ inner tube surface.

In another test, the above-described steam treatment was not carried out, but all other process steps/conditions were essentially the same as in the above-described test. Result: the amount of generated carbon monoxide was 7.1 mole/hour CO per m$^2$ tube surface.

The above-described comparative test results clearly demonstrate that (a) the antifoulant treatment (with dissolved tetrabutyltin) had a significant effect on alleviating CO generation, and (b) steam treatment after antifoulant treatment but before thermal hydrocarbon cracking resulted in an increased effectiveness of the antifoulant (in terms of alleviating the formation of carbon monoxide).

EXAMPLE III

This example illustrates the beneficial effect of injecting a tin-containing antifoulant solution at a relatively low temperature of about 1000°–1300° F. before introducing the steam/ethane feed gas (having a steam:ethane mole ratio of 0.5:1) into the cracking tube and then increasing the operating temperature to about 1450°–1550° F. All tests were carried out in a pilot plant cracking tube reactor, essentially as described in the Example II.

In one test run, a 0.04 molar tetrabutyltin solution in hexane was injected into the ethane thermal cracking tube at a constant temperature of about 1500° F. for about 150 minutes at a rate as to provide a tin-concentration in the feed gas of 42 ppmv Sn. The amount of CO generated in this plant test was 4.7 mole/hour CO per m$^2$ inner tube surface.

In another test, the tetrabutyltin solution was injected into the ethane/steam feed gas stream flowing through the thermal cracking tube, at a temperature starting at about 1250° F. The temperature was then gradually raised to about 1500° F. over a period of about 150 minutes. The antifoulant feed rate was such that the level of Sn in the feed gas during the operation was about 50 ppmv Sn. The amount of CO generated in this plant test was only 0.8 mole/hour CO per m$^2$ inner tube surface, thus demonstrating a beneficial effect of this temperature "ramping" method.

A preliminary laboratory test (not described herein) indicates that a further reduction in CO generation can be attained when the antifoulant solution is injected at an even lower temperature (1050° F. at which no significant cracking occurs), before the temperature is raised to the effective thermal cracking temperature of about 1500° F. (or higher).

Reasonable variations, modifications and adaptions for various usages and conditions can be made within the scope of the disclosure and the appended claims, without departing from the scope of this invention.

That which is claimed is:

1. In a process for injecting a liquid tin-containing antifoulant composition into a metal-walled thermal cracking reactor tube concurrently with the flow of a gaseous stream through said reactor tube, the improvement which comprises injecting said antifoulant composition into said reactor tube through a nozzle being located at the end of a tubular injection quill which is positioned substantially parallel to the flow of said gaseous stream and which extends into the center region of said reactor tube at a distance equal to at least the diameter of said reactor tube.

2. A process in accordance with claim 1, wherein said distance is about 1–3 times the diameter of said reactor tube.

3. A process in accordance with claim 1, wherein said gaseous stream comprises at least one saturated hydrocarbon containing 2–12 carbon atoms per molecule.

4. A process in accordance with claim 3, wherein said gaseous stream comprises steam and at least one saturated hydrocarbon selected from the group consisting of ethane, propane, n-butane and isobutane.

5. A process in accordance with claim 4, wherein the conditions in said reactor tube are such as to affect thermal cracking of said at least one saturated hydrocarbon to at least one unsaturated hydrocarbon.

6. A process in accordance with claim 5, wherein said at least one saturated hydrocarbon is ethane and said antifoulant composition is a solution of tetra-n-butyltin.

7. A process in accordance with claim 1 comprising the additional steps of interrupting the injection of said antifoulant composition while maintaining the flow of said gaseous stream; withdrawing said injection quill past a gate valve; closing said gate valve; cleaning said injection quill or, alternatively, replacing said injection quill with another one; reinserting the cleaned or, alternatively, replaced injection quill past said gate valve which is opened; and reinjecting said antifoulant composition into said reactor tube.

8. In a process for injecting a liquid tin-containing antifoulant composition into a metal-walled thermal cracking reactor tube, the improvement which comprises:
   (1) passing a gaseous stream through said reactor tube while simultaneously injecting said antifoulant composition through a nozzle being located at the end of a tubular injection quill into the reactor tube, wherein said tubular injection quill is positioned substantially parallel to the flow of said gaseous stream and extends into the center region of said reactor at a distance equal to at least the diameter of said reactor tube, at a temperature in the range of about 1000° F. to about 1300° F.; and
   (2) raising the temperature in said reactor tube from the operating temperature of step (1) to a temperature of about 1400°-1800° F., while maintaining the injection of said antifoulant composition through said nozzle and the flow of said gaseous stream through said reactor.

9. A process in accordance with claim 8, wherein the temperature in step (1) is about 1200°-1300° F., and the temperature in step (2) is about 1450°-1550° F.

10. A process in accordance with claim 8, wherein said gaseous stream comprises at least one saturated hydrocarbon containing 2-12 carbon atoms per molecule.

11. A process in accordance with claim 10, wherein said gaseous stream comprises steam and at least one saturated hydrocarbon selected from the group consisting of ethane, propane, n-butane and isobutane.

12. A process in accordance with claim 10, wherein essentially no thermal cracking of said at least one saturated hydrocarbon occurs in step (1), and thermal cracking of said at least one saturated hydrocarbon to at least one unsaturated hydrocarbon occurs in step (2).

13. A process in accordance with claim 12, wherein steam is present in steps (1) and (2), said at least one saturated hydrocarbon is selected from the group consisting of ethane, propane, n-butane and isobutane, and said at least one unsaturated hydrocarbon is selected from the group consisting of ethylene, propylene, butene-1, butene-2 and isobutylene.

14. A process in accordance with claim 13, wherein said at least one saturated hydrocarbon is ethane, said at least one unsaturated hydrocarbon is ethylene, and said liquid antifoulant composition is dissolved tetra-n-butyltin.

15. In a process for injecting a liquid tin-containing antifoulant composition into a metal-walled thermal cracking reactor tube, the improvement which comprises:
   (1) passing a gaseous stream through said reactor tube while simultaneously injecting said antifoulant composition through a nozzle being located at the end of a tubular injection quill into said reactor tube, wherein said tubular injection quill is positioned substantially parallel to the flow of said gaseous stream and extends into the center region of said reactor at a distance equal to at least the diameter of said reactor tube, at a temperature in the range of about 1000° F. to about 1300° F.,
   (1A) interrupting the injection of said antifoulant composition and the flow of said gaseous stream,
   (1B) introducing steam into said reactor tube for at least about 60 minutes at a temperature of about 1000°-1300° F.,
   (1C) interrupting the flow of steam,
   (1D) resuming the injection of said antifoulant composition and the flow of said gaseous stream, and
   (2) raising the temperature in said reactor tube from the operating temperature of step (1) to a temperature of about 1400°-1800° F., while maintaining the injection of said antifoulant composition through said nozzle and the flow of said gaseous stream through said reactor.

16. A process in accordance with claim 15, wherein said gaseous stream comprises at least one saturated hydrocarbon containing 2-12 carbon atoms per molecule.

17. A process in accordance with claim 16, wherein said gaseous stream comprises steam and at least one saturated hydrocarbon selected from the group consisting of ethane, propane, n-butane and isobutane.

18. A process in accordance with claim 15, wherein steam flows in step (1B) for 1-5 hours at a rate of about 1-5000 lb/hour.

19. In a process for injecting a liquid tin-containing antifoulant composition into a metal-walled thermal cracking reactor tube, the improvement which comprises:
   (1) passing a gaseous stream through said reactor tube while simultaneously injecting said antifoulant composition through a nozzle being located at the end of a tubular injection quill into the reactor tube at a temperature in the range of about 1000° F. to about 1300° F.; and
   (2) raising the temperature in said reactor tube from the operating temperature of step (1) to a temperature of about 1400°-1800° F., while maintaining the injection of said antifoulant composition through said nozzle and the flow of said gaseous stream through said reactor;
   wherein said tubular injection quill is positioned substantially parallel to the flow of said gaseous stream and extends into the center region of said reactor tube at a distance equal to at least the diameter of said reactor tube.

20. A process in accordance with claim 19, wherein said distance is about 1-3 times the diameter of said reactor tube, and said gaseous stream comprises steam and at least one saturated hydrocarbon selected from the group consisting of ethane, propane, n-butane and isobutane.

21. In a process for injecting a liquid tin-containing antifoulant composition into a metal-walled thermal cracking reactor tube, the improvement which comprises:
(1) passing a gaseous stream through said reactor tube while simultaneously injecting said antifoulant composition through a nozzle located at the end of a tubular injection quill into said reactor tube at a temperature in the range of about 1000° F. to about 1300° F.,
(1A) interrupting the injection of said antifoulant composition and the flow of said gaseous stream,
(1B) introducing steam into said reactor tube for at least about 60 minutes at a temperature of about 1000°-1300° F.,
(1C) interrupting the flow of steam,
(1D) resuming the injection of said antifoulant composition and the flow of said gaseous stream, and
(2) raising the temperature in said reactor tube from the operating temperature of step (1) to a temperature of about 1400°-1800° F., while maintaining the injection of said antifoulant composition through said nozzle and the flow of said gaseous stream through said reactor;
wherein said tubular injection quill is positioned substantially parallel to the flow of said gaseous stream and extends into the center region of said reactor tube at a distance equal to at least the diameter of said reactor tube.

22. A process in accordance with claim 21, wherein said distance is about 1-3 times the diameter of said reactor tube, and said gaseous stream comprises steam and at least one saturated hydrocarbon selected from the group consisting of ethane, propane, n-butane and isobutane.

* * * * *